US008812099B2

(12) United States Patent
Asirvatham et al.

(10) Patent No.: US 8,812,099 B2
(45) Date of Patent: Aug. 19, 2014

(54) DETECTING AND TREATING NERVOUS SYSTEM DISORDERS

(71) Applicant: Mayo Foundation for Medical Education and Research, Rochester, MN (US)

(72) Inventors: Samuel J. Asirvatham, Rochester, MN (US); Paul A. Friedman, Rochester, MN (US); Charles J. Bruce, Rochester, MN (US); David R. Holmes, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/679,167

(22) Filed: Nov. 16, 2012

(65) Prior Publication Data

US 2013/0079616 A1    Mar. 28, 2013

Related U.S. Application Data

(60) Continuation of application No. 13/468,337, filed on May 10, 2012, now abandoned, which is a division of application No. 12/094,704, filed as application No. PCT/US2006/044958 on Nov. 21, 2006, now Pat. No. 8,204,600.

(60) Provisional application No. 60/738,718, filed on Nov. 22, 2005.

(51) Int. Cl.
*A61N 1/05* (2006.01)
*A61B 5/00* (2006.01)

(52) U.S. Cl.
USPC ........................................ 600/544; 600/378

(58) Field of Classification Search
USPC ................................................. 600/544, 378
See application file for complete search history.

(56) References Cited

U.S. PATENT DOCUMENTS 5,159,928 A    11/1992  Keppel
5,797,849 A     8/1998  Vesely
(Continued)

FOREIGN PATENT DOCUMENTS

WO    WO9952430 A1    10/1999

OTHER PUBLICATIONS

European Search Report in Application No. 13181562.3, dated Oct. 15, 2013, 7 pages.
(Continued)

*Primary Examiner* — Michael Kahelin
*Assistant Examiner* — Alyssa M Alter
(74) *Attorney, Agent, or Firm* — Fish & Richardson P.C.

(57) ABSTRACT

Some embodiments of a mapping device may be capable of passing through cerebral veins and other cerebrovascular spaces to provide electrophysiological mapping of the brain. These embodiments of the device may also be capable of providing, simultaneously or separately, ablation energy or other treatments to targeted brain tissue. In such circumstances, a user may be enabled to analyze an electrophysiological map of a patient's brain and, at the same time or within a short time period before or after the mapping process, may be enabled to apply ablation energy for treatment of a central nervous system disorder. Such treatment may be accomplished without the use of invasive surgery in which the brain is accessed through an opening in the patient's cranium.

19 Claims, 12 Drawing Sheets

(56) References Cited

U.S. PATENT DOCUMENTS

| | | | |
|---|---|---|---|
| 5,908,385 A * | 6/1999 | Chechelski et al. | 600/374 |
| 5,941,251 A | 8/1999 | Panescu | |
| 6,071,279 A | 6/2000 | Whayne et al. | |
| 6,128,538 A | 10/2000 | Fischell et al. | |
| 6,360,122 B1 | 3/2002 | Fischell | |
| 6,648,880 B2 | 11/2003 | Chauvet et al. | |
| 2002/0198521 A1 | 12/2002 | Maguire | |
| 2005/0137647 A1 | 6/2005 | Wallace | |
| 2005/0171525 A1 | 8/2005 | Rioux | |
| 2005/0187589 A1 | 8/2005 | Wallace et al. | |
| 2008/0027346 A1 | 1/2008 | Litt et al. | |

OTHER PUBLICATIONS

European Office Action in European Application No. 06838112.8, dated Aug. 23, 2011, 4 pages.

International Search Report & Written Opinion in International Application No. PCT/US2006/044958, mailed Mar. 28, 2007, 13 pages.

International Preliminary Report on Patentability in International Application No. PCT/US2006/044958, mailed Jun. 5, 2008, 8 pages.

Luguet et al., NPY/AgRP neurons are essential for feeding in adult mice but can be ablated in neonates, *Science*, 2005, 310: 683-685.

Spencer, "Electric shock makes a comeback," Wall Street Journal Personal Journal, 2005, pp. D1-D5.

\* cited by examiner

Over the Wire Mapping and Ablation

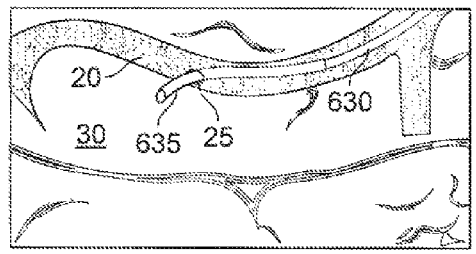
FIG. 6B — Needle Perforation
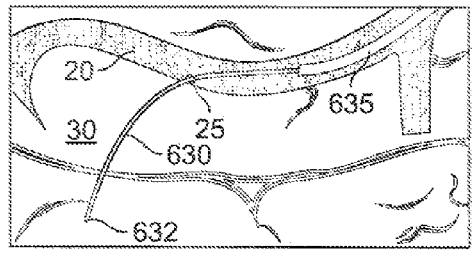
FIG. 6C — Wire Advanced, Needle Withdrawn
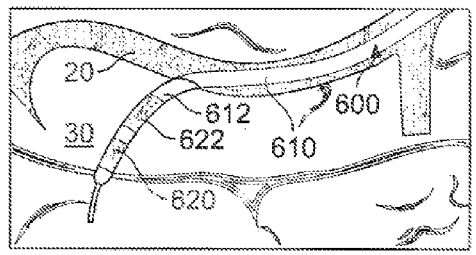
FIG. 6D — Catheter Advanced
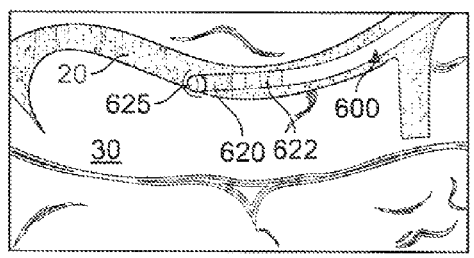
FIG. 6E — Catheter withdrawal with ablation

DETECTING AND TREATING NERVOUS SYSTEM DISORDERS

CROSS REFERENCE TO RELATED APPLICATION(S)

This application is a continuation of U.S. application Ser. No. 13/468,337 and entitled "Detecting And Treating Nervous System Disorders," which is a division of U.S. application Ser. No. 12/094,704 and entitled "Detecting And Treating Nervous System Disorders," which is a national stage application under 35 U.S.C. §371 that claims the benefit of PCT/US2006/044958 filed on Nov. 21, 2006 and entitled "Detecting And Treating Nervous System Disorders," which claims priority to U.S. Provisional Application Ser. No. 60/738,718 filed on Nov. 22, 2005 by Asirvatham et al. and entitled "Detecting And Treating Nervous System Disorders," the contents of these previous applications are incorporated herein by reference.

TECHNICAL FIELD

This document relates to detection and treatment of one or more nervous system disorders.

BACKGROUND

Some disorders of the nervous system may be traced to particular portions of the brain. For example, Epilepsy is a nervous system disorder that can cause seizures due to abnormal electrical activity in a particular portion of the brain. Epilepsy affects approximately 50,000 to 100,000 people per year in the United States and is known to affect people of all age groups.

The abnormal electrical activity that occurs in the brain during an Epileptic seizure may be focused in the different portions of the brain depending upon the patient. As such, a patient's brain may be "mapped" to determine a particular portion of the brain that requires treatment. The mapping process may be accomplished using electroencephalogram (EEG) sensors placed on the outside of the patient's scalp, using magnetic resonance imaging (MRI) technique, or using electrocorticography (ECoG) electrodes placed on the outside of the brain through an opening formed in the patient's cranium. In general, the noninvasive methods of mapping the brain provide limited resolution compared to the more invasive methods that require access to the brain through a opening formed in the cranium, yet these invasive methods are often associated with a prolonged recovery period and an increased risk of morbidity.

Epilepsy and some other nervous system disorders can be treated with drug therapy or surgery. In many cases, the drugs are not fully effective for purposes of treating the disorder (e.g., epileptic seizures may still occur even with the treatment of drug therapy). Also, some of the drugs used to treat the nervous system disorder may have harmful or undesirable side effects.

Surgical treatment for Epilepsy and other nervous system disorders typically requires a surgeon to cut an opening in the patient's cranium. After the targeted area has been determined (e.g., using a mapping technique), the surgeon may remove the targeted brain tissue through the opening formed in the patient's cranium. Alternatively or in addition, the surgeon may insert electrodes through the opening in the patient's cranium into the targeted brain tissue to provide electrical stimulation to that area of the brain. For example, deep brain stimulation (DBS) is a technique, conventionally used to treat Parkinson's Disease and other nervous system disorders, in which the stimulation electrode is advanced through the opening in the patient's cranium to the thalamus or other area deep in the brain. These surgical techniques may be significantly invasive (e.g., requires an opening formed in the patient's cranium or requires access to the brain via the cerebrospinal fluid), which typically results in prolonged recovery times and, in some circumstances, an increased risk of morbidity.

SUMMARY

Some embodiments of a mapping device may be capable of passing through cerebral veins and other cerebrovascular spaces to provide electrophysiological mapping of the brain. These embodiments may also be capable of providing, simultaneously, sequentially, or separately, ablation energy (e.g., RF energy, ultrasound energy, microwave energy, or the like) or other treatments to targeted brain tissue. In such circumstances, a user may be enabled to analyze an electrophysiological map of a patient's brain and, at the same time or within a short time period before or after the mapping process, may be enabled to apply ablation energy for treatment of a nervous system disorder. Such treatment may be accomplished without the use of invasive surgery in which the brain is accessed through an opening in the patient's cranium. Furthermore, in some circumstances, such access to the brain may allow early detection of an impending vascular event (e.g., a stroke) or electrical event (e.g., a seizure).

In some embodiments, an electrophysiological brain mapping device may include an elongated body having a distal end to pass through one or more cerebral veins proximal to brain tissue. The elongated body may define a fluid input conduit in fluid communication with a fluid input port near the distal end and may be a drain conduit in fluid communication with a drain port near the distal end. The device may also include one or more electrodes to detect electrophysiological signals in a portion of the brain and to deliver ablation energy. The electrodes may be disposed near the distal end of the elongated body. The device may further include a balloon structure disposed near the distal end so as to surround the fluid input port, the drain port, and the electrodes. The balloon structure may be adjustable from a non-expanded state to an expanded state when a fluid flows from the input port and to the drain port.

In other embodiments, an implantable control device for predicting an imminent event in a brain may include a housing implantable in a body of a patient. The device may also include a controller circuit at least partially disposed in the housing. The controller circuit may comprise at least one filter to receive electrophysiological signals detected by one or more electrodes disposed in a portion of a brain. The device may further include a wireless transmitter to transmit a signal to a device outside the body of the patient in response to abnormal brain activity detected by the electrodes. The wireless transmitter may be electrically coupled to the controller circuit.

These and other embodiments may provide one or more of the following advantages. First, some embodiments of the devices and methods described herein provide a noninvasive, high-resolution process of mapping particular portions of the brain. For example, the use of EEG electrode placed on the outside of a patient's scalp provides a noninvasive process for mapping the patient's brain, but the resolution of the external EEG monitoring process is not as detailed as the more invasive ECoG process in which electrodes are placed directly on the brain through an opening in the patient's cranium (e.g., a significant portion of the signal "spikes" sensed by the ECoG process are not sensed by the EEG process). As described in more detail below, some embodiments of the devices and methods described herein provide a noninvasive process for disposing sensor electrodes (e.g., EEG electrodes or the like) and for mapping at least a portion of the brain with substantially higher resolution that typical external mapping processes. Moreover, the devices and method described herein permit such high resolution mapping of the brain without necessarily requiring surgery in which an opening is formed in the patient's cranium. As such, the patient recovery time may be substantially reduced and, in some circumstances, the risk of morbidity may be substantially reduced.

Second, the devices and methods described herein may provide for contemporaneous mapping and treatment or at least a portion of the brain. For example, a catheter device may be used to deliver electrodes to the brain for sensing electrical signals to map the brain, and the catheter device may also include instrumentation for ablating or otherwise treating brain tissue affected by a nervous system disorder (e.g., Epilepsy or the like). In such circumstances, the pathological site or targeted brain tissue may be treated without the need for invasive surgery in which brain tissue is cut and removed though an opening formed in the patient's cranium. Thus, the targeted portion of the brain may be contemporaneously mapped and treated in a manner that can substantially reduce the patient recovery time and the risk of morbidity. The high resolution afforded by the mapping is also applied to the treatment, which is focally delivered to affect target tissues with a reduced likelihood of collateral tissue damage. While epilepsy may be referred to frequently in this document, it should be understood that many conditions including dyslexia or memory disruption, obsessive-compulsive disorder, depression, and others may have similar localized electrical conditions as their mechanism. The mapping and therapy techniques described herein may apply to sufferer's of these conditions as well.

Third, the devices and methods described herein may nonsurgically deliver electrodes and/or treatment instrumentation to the brain using cerebral veins and other cerebrovascular spaces. Delivering the electrodes through the venous system (which is generally a lower pressure environment) may reduce the risk of bleeding or stroke the procedures described herein. For example, such low pressure vessels may act as a conduit to permit catheter placement of electrodes adjacent to target tissues. If closer placement is required, these low pressure vessels may be exited. In some circumstances, venous travel minimized the amount of nervous tissue that must be traversed before therapy delivery. Thus, in some embodiments, a user may nonsurgically deliver electrodes and/or treatment instrumentation to targeted portions of the brain, including portions in the frontal lobe, parietal lobe, occipital lobe, temporal lobe, thalamus, hypothalamus, and the like. For example, some of the devices described herein may be capable of targeting and ablating neurons in the arcuate nucleus of the hypothalamus so as to treat obesity or other conditions.

Fourth, some embodiments of the catheter device may employ a cooling system to both internally cool the catheter and to externally cool the surrounding the distal end of the catheter. This dual-action cooling catheter may permit greater ablation energy, such as heat, to be delivered to targeted portions of the brain with causing excess damage to non-targeted portions. While therapy to nervous tissues is discussed herein, it should be understood that this type of dual-action cooling catheter may be useful in many applications in medicine, such as the ablation energy treatment of fatty tissues or in regions of limited blood flow.

Fifth, some embodiments of the devices and methods described herein may include an implantable control unit that is electrically coupled to the sensor electrodes delivered to the brain. As previously described, the sensor electrodes may be capable of providing a high resolution map of the electrophysiological signals of at least a portion of the brain. In response to these signals or in response to other inputs, the implantable control unit include computer-implemented program to predict an imminent vascular event (e.g., a stroke) or electrical event (e.g., a seizure). Detection of an imminent event may be provided, in some embodiments, by detection of changes in electrical nervous activity that antecede the clinical event (e.g. pre-seizure electrical changes), by detection of changes in electrical events cause by ischemia (before frank stroke occurs), or by recording other modalities. Other such modalities could include Doppler signals of the arteries to the brain (which lie adjacent to the veins used by these implantable devices). Moreover, in some embodiments, the control unit may be configured to treat (e.g., deliver a medicament, deliver electrical stimulation, deliver ablation energy, or the like) a particular portion of the brain in response to the sensor signals from the electrodes or in response to the prediction of the imminent vascular event or electrical event. Other therapies provided by the control unit may include bursts of rapid, painless pacing to "reset" the fast electrical activity giving rise to a seizure, or delivery of a low energy shock via electrodes placed venously proximate to nervous tissue so that a small energy delivery would suffice. Alternatively, in other embodiments, rather than therapy, patient warning (e.g., an audible alert, a small shock, or a GPS-based signal to a medical service) could be issued.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-E is a side view of a mapping-ablation device being advanced toward targeted brain tissue, in accordance with certain embodiments of the invention.

DETAILED DESCRIPTION OF ILLUSTRATIVE EMBODIMENTS

Figure 1:
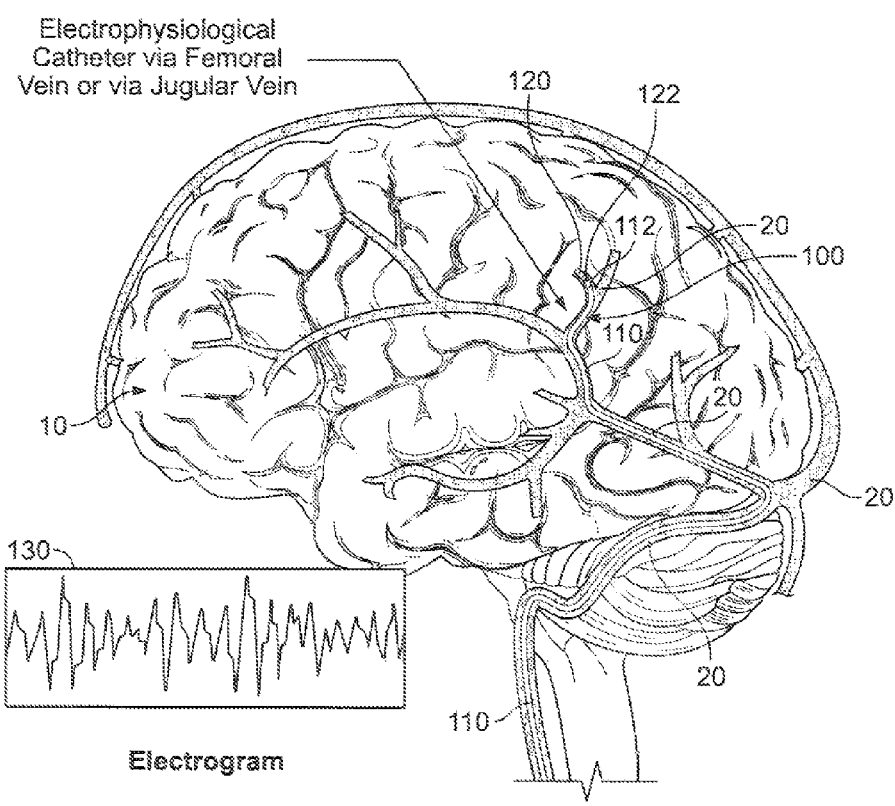
FIG. 1 is a side view of a mapping electrode device delivered through a vein to a brain, in accordance with some embodiments of the invention.

Referring to FIG. 1, some embodiments of a mapping electrode device 100 may include an elongated body 110 and one or more electrodes near a distal end 112 of the elongated body 110. In this embodiment, the device 100 includes two electrodes 120 and 122 that are capable of detecting electrophysiological signals in a portion of a brain 10, capable of detecting impedance parameters in a portion of the brain 10, or both. The elongated body 110 may comprise a flexible, biocompatible material so that the electrodes 120 and 122 may be delivered be delivered to a targeted portion of the brain via cerebral veins 20 or other cerebrovascular spaces. As such, the electrodes 120 and 122 of the mapping electrode device 100 may provide a relatively high-resolution process of mapping particular portions of the brain 10 without the use of invasive surgery in which the brain 10 is accessed through an opening in the patient's cranium.

The elongated body 110 may comprise a flexible catheter having a conduit through which one or more electrical wires or conductive lines (not shown in FIG. 1) may pass. The electrical wires may extend through the elongated body 110 so as to electrically couple to the electrodes 120 and 122 near the distal end 112 of the body 110. As described in more detail below, the electrical wires may extend out of a proximal end (not shown in FIG. 1) of the elongated body 110 so as to electrically couple with a control unit, such as an electrophysiological mapping control and display system or an implantable control unit (described in more detail below).

The distal end 112 of the elongated body 110 may percutaneously enter the patent's venous system via the femoral vein or via the jugular vein. For example, the device 100 depicted in FIG. 1 may percutaneously enter into the patient's jugular vein and then pass through one or more cerebral veins 20 into a particular portion of the patient's brain 10. The distal end 112 of the elongated body 110 may be steerable so that the electrodes 120 and 122 may be delivered to the targeted portion of the brain (e.g., the parietal lobe, the temporal lobe, the occipital lobe, the frontal lobe, the thalamus, or the like) through one or more cerebral veins 20. For example, the device 100 may include a shape-memory member or one or more steering wires to cause the distal end 112 to bend in a particular direction. As such, a user may steer the distal end 112 of the elongated body 110 into a desired vein, thereby directing the electrodes 120 and 122 to a particular portion of the brain 10. In another example, the device 100 may include a conduit or lumen extending therethrough that is capable of sliding over a guide wire. As such, the distal end 112 of the device 100 may include a conduit opening to receive a guide wire that was previously delivered to the targeted portion of the patient's brain 10. The user may then deliver the electrodes 120 and 122 to the targeted portion by sliding the device 100 over the guide wire. In these embodiments, the outer diameter of the elongated body 110 may be sized to safely pass through the inside of various cerebral veins 20.

In one implementation, the mapping electrode device 100 may percutaneously enter the venous system through the patient's jugular vein. From there, the user may direct the distal end 112 of the elongated body 110 through one or more cerebral veins 20 toward a targeted portion of the patient's brain 10. In this embodiment, the distal end 112 is directed to a portion of the brains' parietal lobe. When the mapping electrode device 100 is delivered to the targeted portion of the brain 10, the one or more electrical wires may extend out from proximal end (not shown in FIG. 1) of the elongated body and may be connected to an electrophysiological mapping and display system (e.g., a digital EEG display system or the like) located near the patient's body. In such circumstances, the electrodes 120 and 122 disposed in a portion of the patient's brain 10 may detect the electrophysiological signals occurring in that portion of the patient's brain, and such signals may be received by the mapping and display system so that the one or more signals may be viewed in a display screen 130. Accordingly, a user may view a high-resolution map (e.g., greater resolution that a traditional external EEG procedure) of at least a portion of the patient's brain without an invasive procedure that requires an opening to be formed in the patient's cranium. In this example depicted in FIG. 1, two electrodes are described, but it should be understood that the device 100 may employ three or more electrodes along the length of device 100 to permit simultaneous mapping from multiple regions of nervous tissue. In such embodiments, these electrodes may be small to enhance mapping resolution and may be electronically "wired together" to record from a larger area, or when needed for therapy delivery (described in more detail below).

As described in more detail below, some embodiments of the electrode device 100 may be capable of contemporaneously mapping and ablating a targeted portion of the patient's brain 10. In such circumstances, a user may be enabled to analyze an electrophysiological map of a patient's brain and, at the same time or within a short time period before or after the mapping process, may be enabled to apply ablation energy for treatment of a nervous system disorder.

Figure 2:
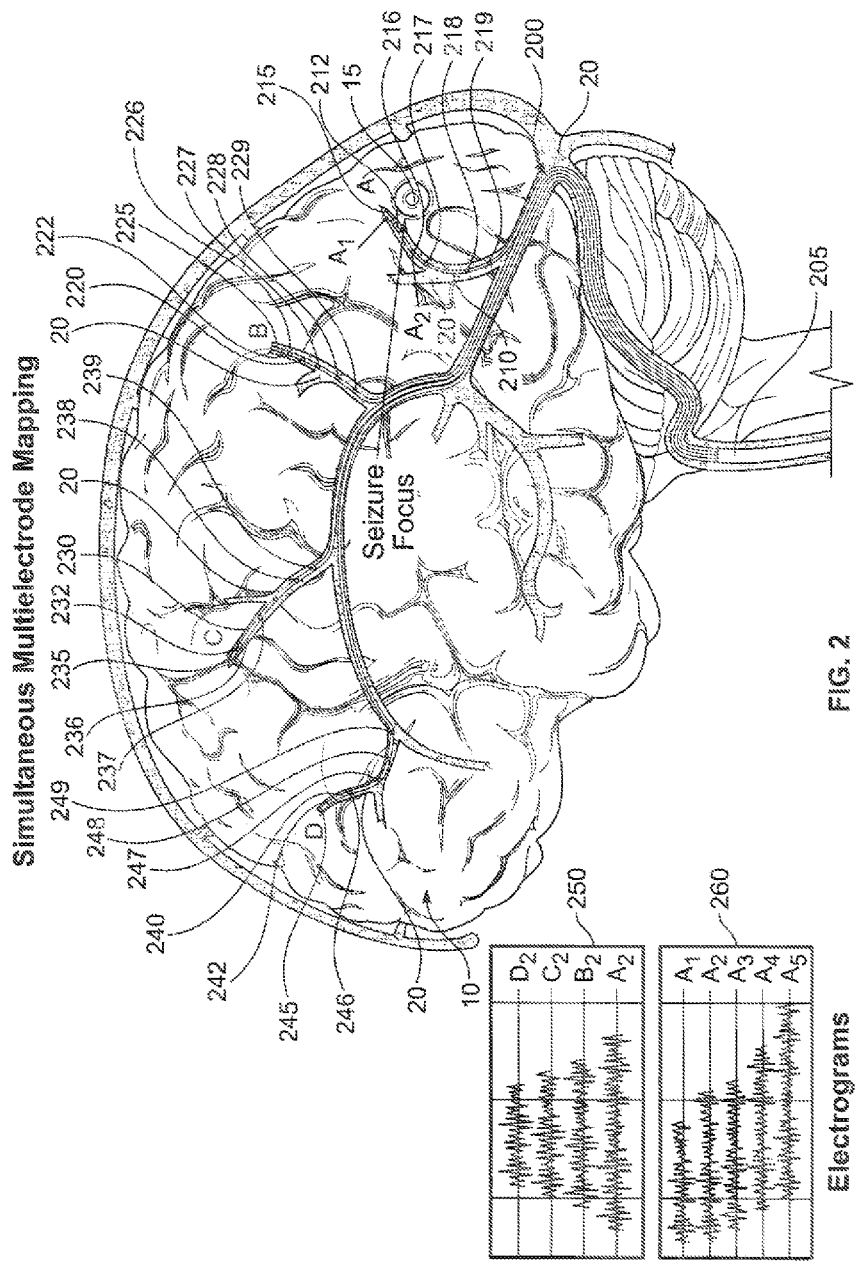
FIG. 2 is a side view of a plurality of mapping electrode devices delivered through the venous system to certain portions of a brain, in accordance with some embodiments of the invention.

Referring to FIG. 2, some embodiments of a mapping electrode device 200 may include a plurality of elongated bodies 210, 220, 230, and 240 that can be separately delivered to different portions of the brain 10. Each of the elongated bodies 210, 220, 230, and 240 may include a plurality of electrodes near the distal end 212, 222, 232, and 242, respectively. (It should be understood that, in some embodiments, the "distal end" may extend quite proximally, so that electrodes span the a substantial portion of the distance the elongated body is in the brain.) For example, the elongated body 210 may include five electrodes 215, 26, 217, 218, and 219 disposed near the distal end 212. As previously described, the five electrodes 215, 26, 217, 218, and 219 may be electrically coupled to one or more wires passing through a conduit in the elongated body 210 so that electrophysiological signals in the brain 10 detected by the five electrodes 215, 26, 217, 218, and 219 may be transmitted to an implantable control unit or an electrophysiological mapping and display system (e.g., a digital EEG display system or the like).

The other elongated bodies 220, 230, and 240 may also include associated electrodes. In this non-limiting example, elongated body 220 may include five electrodes 225, 226, 227, 228, and 229 near its distal end 222. Also, elongated body 230 may include five electrodes 235, 236, 237, 238, and 239 near its distal end 232. Further, elongated body 240 may include five electrodes 245, 246, 247, 248, and 249 near its distal end 242. The electrodes disposed on the elongated bodies 220, 230, and 240 may be electrically coupled to one or more wires passing through a conduit in the associated elongated body. As such, electrophysiological signals in the brain 10 detected by the electrodes disposed on the elongated bodies 220, 230, and 240 may be transmitted to an implantable control unit or an electrophysiological mapping and display system (e.g., a digital EEG display system or the like).

Still referring to FIG. 2, each of the elongated bodies 210, 220, 230, and 240 may comprise a flexible, biocompatible material so that the electrodes disposed thereon may be delivered be delivered to a targeted portion of the brain via cerebral veins 20 or other cerebrovascular spaces. For example, the elongated bodies 210, 220, 230, and 240 may comprise flexible catheters having at least one conduit through which one or more electrical wires or conductive lines (not shown in FIG. 2) may pass. As previously described, the electrodes disposed near the distal end of each the elongated bodies 210, 220, 230, and 240 may provide a relatively high-resolution map of particular portions of the brain 10 without the use of invasive surgery in which the brain 10 is accessed through an opening formed in the patient's cranium.

The distal ends 212, 222, 232, and 242 of the elongated bodies 210, 220, 230, and 240 may percutaneously enter the patent's venous system via the femoral vein or via the jugular vein. For example, the device 200 depicted in FIG. 2 may include a guide catheter 205 that percutaneously enters into the patient's jugular vein and then passes toward one or more cerebral veins 20.

Then, one of the elongated bodies 210, 220, 230, and 240 may be delivered into the jugular vein through the guide catheter 205 and toward a targeted portion of the brain 10. For example, the distal end 242 of the elongated body 240 may be delivered to a frontal lobe portion of the brain 10 before the other elongated bodies 230, 220, and 210 are delivered to other portions of the brain through the guide catheter 205.

Still referring to FIG. 2, the distal ends 212, 222, 232, and 242 of the elongated bodies 210, 220, 230, and 240 may be steerable so that the electrodes disposed thereon may be delivered to the targeted portion of the brain through one or more cerebral veins 20. As previously described, each of the elongated bodies 210, 220, 230, and 240 may include a shape-memory member or one or more steering wires to cause the distal end to bend in a particular direction. As such, a user may steer the distal end 212, 222, 232, or 242 into a desired vein, thereby directing the associated electrodes to a particular portion of the brain 10. In another example, each of the elongated bodies 210, 220, 230, and 240 may include a conduit extending therethrough that is capable of sliding over a guide wire. As such, the distal ends 212, 222, 232, and 242 may include a conduit opening to receive an associated guide wire that was previously delivered to the targeted portion of the patient's brain 10. In these embodiments, the outer diameter of the elongated bodies 210, 220, 230, and 240 may be sized so that a plurality of the elongated bodies 210, 220, 230, and 240 may pass side-by-side through the inside of various cerebral veins 20.

In one exemplary implementation, the mapping electrode device 200 may percutaneously enter the venous system through the patient's jugular vein. From there, the user may direct the distal ends 212, 222, 232, and 242 of the elongated bodies 210, 220, 230, and 240 through one or more cerebral veins 20 toward their respective targeted portions of the patient's brain 10. In this embodiment, the distal end 242 of one elongated body 240 (labeled as "D" in FIG. 2) is directed to a frontal lobe portion of the brain 10, the distal ends 232 and 222 of the elongated bodies 230 and 220 (labeled as "C" and "B" in FIG. 2) are directed to different areas in a parietal lobe portion of the brain 10, and the distal end 212 of the elongated body 210 (labeled as "A" in FIG. 2) is directed to an occipital lobe portion of the brain 10. When the mapping electrode device 200 is delivered to the multiple targeted portions of the brain 10, the one or more electrical wires may extend out from proximal ends (not shown in FIG. 2) of the elongated bodies 210, 220, 230, and 240 and may be connected to an electro-physiological mapping and display system (e.g., a digital EEG display system or the like) located near the patient's body.

As previously described, the electrodes disposed in targeted portions of the patient's brain 10 may detect the electrophysiological signals occurring in that portion of the patient's brain, and such signals may be received by the mapping and display system so that the one or more signals may be viewed in display screens 250 and 260. For example, a first display screen 250 may display the electrophysiological signals detected by electrodes in different portions of the brain 10. The second display screen 260 may display the signals detected by electrodes disposed 215, 216, 217, 218, and 219 on the same elongated body 210. In such circumstances, the first screen 250 may display signals the provide an electrophysiological map of the brain 10 while the second screen 260 permits a user to focus on the signals detected near an electrical event, such as a seizure focus 215. By providing a map of different portions of the brain, a user may be capable of detecting which portion is experiencing an electrical event (e.g., a seizure focus 215), and the user may refer to the second screen 260 to provide a more detailed analysis of the electrophysiological map in that particular portion of the brain 10. Such a detailed analysis may provide the user with an opportunity to accurately determine the coordinates of the brain portion that requires treatment, such as ablation energy to a specific portion of the brain 10. Again, the mapping electrode device 200 may provide a high-resolution map (e.g., greater resolution that a traditional external EEG procedure) of different portions of the patient's brain 10 without an invasive procedure that requires an opening to be formed in the patient's cranium.

Furthermore, the relative anatomic positions of each of the elongated bodies (210, 220, 230, 240) may be known by a number of techniques. One such technique may include placement of unique fluoroscopic markers on each elongated body to permit its radiographic identification while deployed in the brain. In another technique, an electrical field is applied externally and recorded on each of the electrodes. The relative strength of the electric fields in each electrode determines its position. Three dimensional localization may be accomplished using orthogonal electric fields of low energy each uniquely encoded with a different frequency or using temporally encoded permit three dimensional localization. These positions of the elongated body can be registered using computer software with previously acquired CT or MRI images to permit identification of catheter positions with the nervous system. An alternate technique would deliver low energy signals (electrical or ultrasound) from the electrodes to permit their localization by means of relative energy strength at other electrode recording sites. Precise localization would permit selection of specific electrodes for therapy delivery, as described in more detail below.

As described in more detail below, some embodiments of the elongated bodies 210, 220, 230, and 240 may be capable of contemporaneously mapping and ablating a targeted portion of the patient's brain 10. In such circumstances, a user may be enabled to analyze an electrophysiological map of a patient's brain and, at the same time or within a short time period before or after the mapping process, may be able to apply ablation energy for treatment of a nervous system disorder.

Figure 3A:
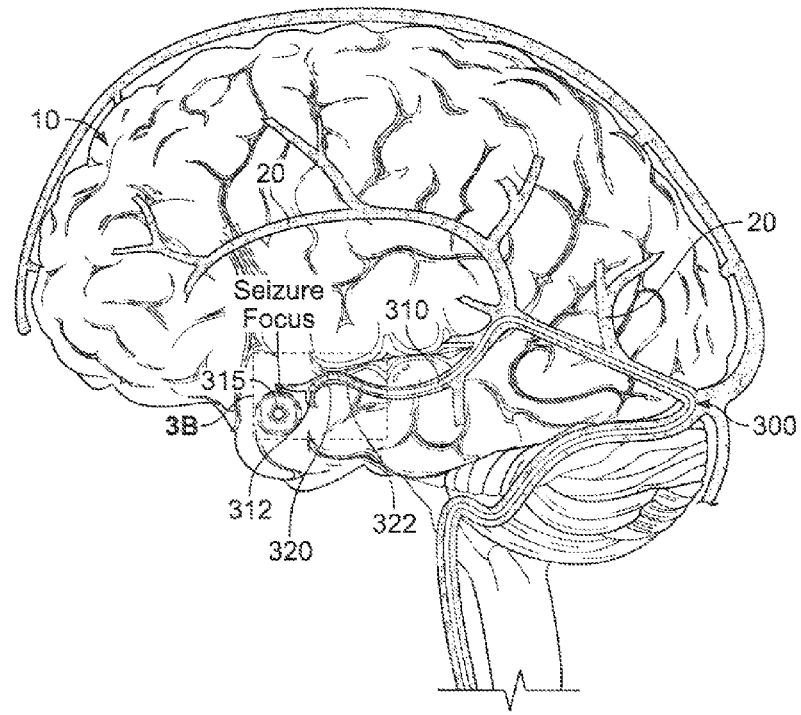
FIGS. 3A-B are a side views of a mapping-ablation device delivered through a vein to a particular portion of a brain, in accordance with some embodiments of the invention.
Figure 3B:
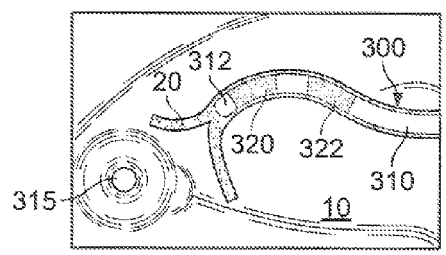

Referring now to FIGS. 3A-B, a mapping-ablation device 300 may include an elongated body 310 and one or more electrodes disposed near a distal end 312 of the elongated body 310. The electrodes may be electrically coupled to one or more wires (or conductive traces) passing through a conduit of the elongated body 310. In such circumstances, the electrodes may be capable of detecting electrophysiological signals in at least a portion of the patient's brain 10 and may be capable of contemporaneously delivering ablation energy to that portion of the brain 10. For example, the electrodes may be configured to deliver radio frequency (RF) ablation energy or ultrasound ablation energy so as to treat a particular portion of the brain 10 that is affected by a nervous system disorder.

In this embodiment, the mapping-ablation device 300 includes two electrodes 320 and 322 disposed near the distal end 312. The electrodes 320 and 322 may be configured to detect electrophysiological signals in at least a portion of the brain 10 and may be configured to contemporaneously delivery RF ablation energy to that portion of the brain. As such, a user may (1) access the targeted portion of the brain 10 via one or more cerebral veins 20, (2) detect signals in at least that portion of the brain 10 so as to view a high-resolution map, (3) deliver ablation energy to that portion of the brain 10 to treat a nervous system disorder, and (4) detect signals in that portion of the brain again to determine the effectiveness of the ablation treatment. Moreover, the user may perform this process or other processes without an invasive procedure that requires an opening to be formed in the patient's cranium.

Still referring to FIGS. 3A-B, the elongated body 310 may comprise a flexible catheter having a conduit through which one or more electrical wires or conductive lines (not shown in FIG. 3) may pass. The electrical wires may extend out of a proximal end (not shown in FIG. 3) of the elongated body 310 so as to electrically couple with a control unit, such as an electrophysiological mapping control and display system or an implantable control unit. The distal end 312 of the elongated body 310 may percutaneously enter the patent's venous system via the femoral vein or via the jugular vein. Also, the distal end 312 of the elongated body 310 may be steerable so that the electrodes 320 and 322 may be delivered to the targeted portion of the brain through one or more cerebral veins 20. For example, the elongated body 310 may include a conduit extending therethrough that is capable of sliding over a guide wire. The user may deliver the electrodes 320 and 322 to the targeted portion of the brain 10 by sliding the elongated body 310 over the guide wire. In such embodiments, the outer diameter of the elongated body 310 may be sized to safely pass through the inside of the cerebral veins 20.

In one exemplary implementation, a user may be able to analyze an electrophysiological map of a patient's brain 10 and, at the same time or within a short time period before or after the mapping process, may be able to apply ablation energy for treatment of a nervous system disorder. As shown in FIGS. 3A-B, the mapping-ablation electrode device 300 may percutaneously enter the venous system through the patient's jugular vein, and the distal end 312 may be directed through one or more cerebral veins 20 toward a targeted portion of the patient's brain 10. (In this embodiment, the distal end 312 is directed to a temporal lobe portion of the brain 10.) The user may direct the electrodes 320 and 322 to different portions of the brain 10 and therein detect the electrophysiological signals to map at least a portion of the brain 10 using, for example, an electrophysiological mapping and display system (e.g., a digital EEG display system or the like). If the mapping process does not reveal a portion of the brain 10 affected by a nervous system disorder, the user may direct the electrodes 320 and 322 to a different portion of the brain 10.

If the mapping process reveals a portion of the brain 10 that is affected by a nervous system disorder of otherwise requires treatment, the user may thereafter deliver ablation energy to the affected tissue using the electrodes 320 and 322. For example, as shown in FIGS. 3A-B, if the mapping process determines the location of an electrical event, such as a seizure focus 315, in the brain 10, the electrodes 320 and 322 may be used to delivery RF ablation energy to the brain tissue in the affected portion of the brain. The RF energy may cause thermal ablation to the targeted tissue and render this tissue electrically inactive, which may prevent future occurrences of the electrical events (e.g., seizure focus 315) associated with the nervous system disorder. Accordingly, in some embodiments, a user may view a high-resolution map of at least a portion of the patient's brain and may contemporaneously treat that portion of the brain with ablation energy, all of which may be accomplished without an invasive procedure that requires an opening to be formed in the patient's cranium.

In an alternate embodiment, multiple electrodes may be disposed on the elongated body as shown in FIG. 2. Once the target tissue is identified, energy is delivered between the two (or more) electrodes that may be situated on any elongated member to select an energy path that treats target tissue while reducing the likelihood of collateral damage to healthy tissues. Such an embodiment may permit high-resolution mapping without necessarily repositioning mapping catheters.

Figure 4:
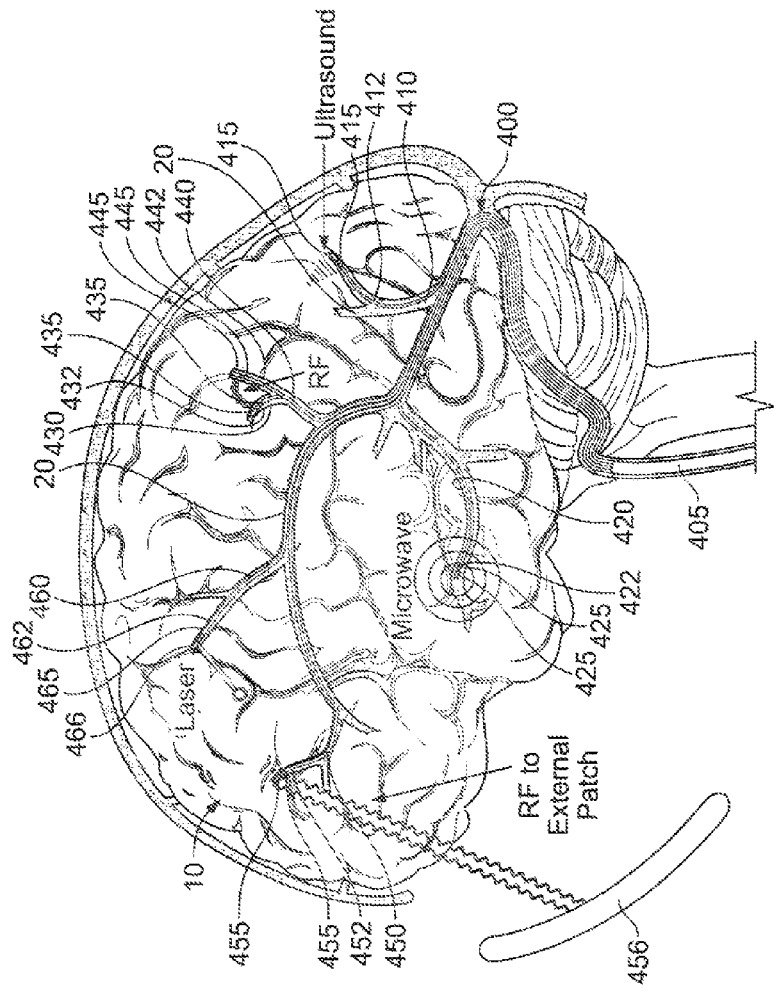
FIG. 4 is a side view of a plurality of a mapping-ablation devices delivered through veins to targeted portions of a brain.

Referring to FIG. 4, some embodiments of a mapping-ablation device 400 may employ different forms of ablation energy depending on the desired treatment, the affected tissue, quantity of energy delivered, and other factors. The mapping ablation devices may include one elongated body or a plurality of elongated members. The mapping-ablation device 400 may include a first elongated body that is equipped to deliver a first type of ablation energy (e.g., RF ablation energy, ultrasound ablation energy, microwave ablation energy, laser ablation energy, or the like) and a second elongated body that is equipped to deliver a different type of ablation energy Alternatively, all of the elongated bodies of the mapping ablation device 400 may be equipped to deliver the same type of ablation energy.

For example, the mapping-ablation device 400 may include at least one elongated body 410 having a distal end 412 and one or more ultrasound ablation transducers 415 disposed thereon. The elongated body may include, in addition to the ultrasound transducers 415, one or more electrodes to map the electrophysiological signals in the brain 10. Alternatively, the mapping electrodes may also serve as the ultrasound transducers 415. In such embodiments, a user may view a high-resolution map of at least a portion of the patient's brain and may contemporaneously treat that portion of the brain with ultrasound ablation energy, all of which may be accomplished without an invasive procedure that requires an opening to be formed in the patient's cranium.

In another example, the mapping-ablation device 400 may include at least one elongated body 420 having a distal end 422 and one or more microwave ablation probes 425 disposed thereon. The elongated body may include, in addition to the microwave ablation probes 425, one or more electrodes to map the electrophysiological signals in the brain 10. Alternatively, the mapping electrodes may also serve as the microwave ablation probes 425. Again, in these embodiments, a user may view a high-resolution map of at least a portion of the patient's brain and may contemporaneously treat that portion of the brain with microwave ablation energy without an invasive procedure that requires an opening to be formed in the patient's cranium.

In further example, the mapping-ablation device 400 may include a first elongated body 430 having a distal end 432 and one or more RF ablation electrodes 435 disposed thereon. Also, the mapping-ablation device 400 may include a second elongated body 430 having a distal end 442 and one or more RF ablation electrodes 445 disposed thereon. In such circumstances, the first and second elongated members may be used to deliver RF ablation energy to the tissue between the two different sets of electrodes 435 and 445. As previously described, the RF electrodes 435 and 445 may also serve as the mapping electrodes so that a user may view a high-resolution map of at least a portion of the patient's brain and may contemporaneously treat that portion of the brain with RF ablation energy.

Still referring to FIG. 4, in yet another example, the mapping-ablation device 400 may include at least one elongated body 450 having a distal end 452 and one or more RF ablation electrodes 455 disposed thereon. As previously described, the RF electrodes 455 and 445 may also serve as the mapping electrodes. The RF electrodes 455 may interact with electrodes on an external patch coupled to the outer surface of the patient's scalp. In such circumstances, the elongated member 450 may be used to deliver RF ablation energy to the tissue between the electrodes 455 and the patch 456. Again, in these embodiments, a user may view a high-resolution map of at least a portion of the patient's brain and may contemporaneously treat that portion of the brain with RF ablation energy without an invasive procedure that requires an opening to be formed in the patient's cranium.

In a further example, the mapping-ablation device 400 may include at least one elongated body 460 having a distal end 462 and at least one more laser ablation device 466 disposed thereon. The elongated body may include, in addition to the laser ablation device 466, one or more electrodes 465 to map the electrophysiological signals in the brain 10. In these embodiments, a user may view a high-resolution map of at least a portion of the patient's brain and may contemporaneously treat that portion of the brain with laser ablation energy without an invasive procedure that requires an opening to be formed in the patient's cranium.

Figure 5A:
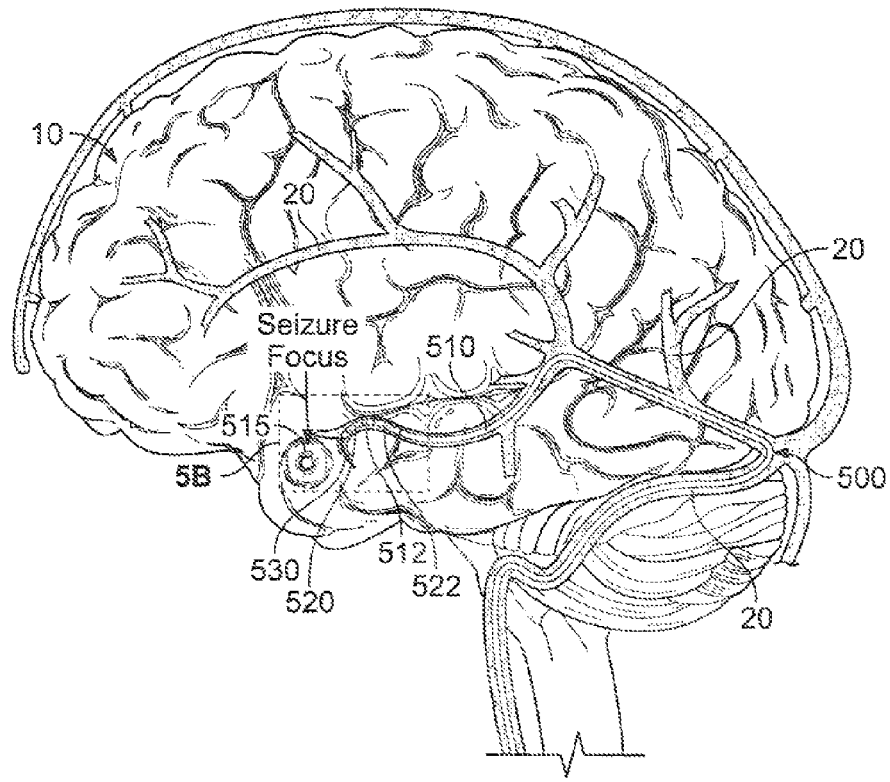
FIG. 5A-B are a side views of another embodiment of a mapping-ablation device delivered through a vein to a particular portion of a brain.
Figure 5B:
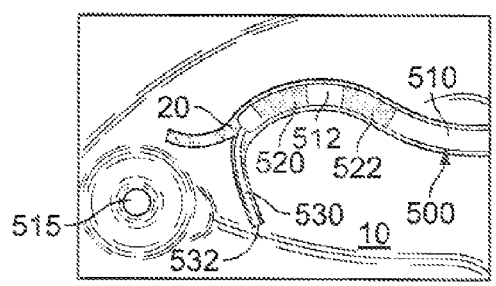
Figure 6A:
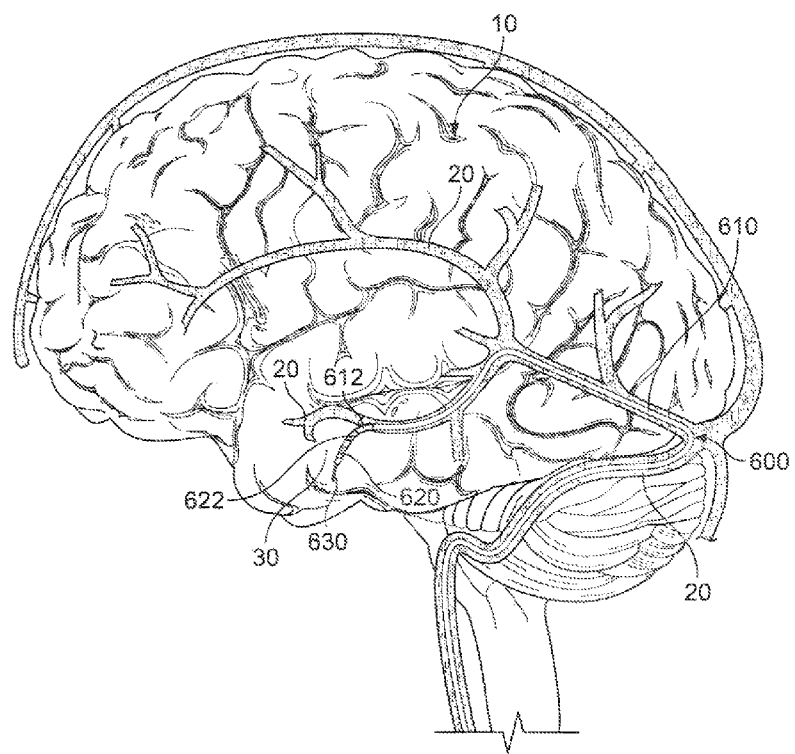

Referring now to FIGS. 5A-B, a mapping-ablation device 500 may include an elongated body 510 that is configured to slide over a guide wire 530 in order to deliver one or more electrodes to a targeted portion of the brain 10. In this embodiment, the device 500 includes two electrodes 520 and 522 that are capable of detecting electrophysiological signals in a portion of a brain 10, capable of detecting impedance parameters in a portion of the brain 10, or both. The elongated body 510 may comprise a flexible catheter having a conduit through which one or more electrical wires or conductive lines (not shown in FIGS. 5A-B) may pass. The electrical wires may extend through the elongated body 510 so as to electrically couple to the electrodes 520 and 522, and the electrical wires may extend out of a proximal end (not shown in FIGS. 5A-B) of the elongated body 510 so as to electrically couple with a control unit, such as an electrophysiological mapping control and display system or an implantable control unit.

The guide wire 530 may comprise a flexible, biocompatible material having a distal end 532 that is steerable or may be controllably bendable. As such, the guide wire 530 may percutaneously enter the patient's jugular or femoral vein and then may be directed to a targeted portion of the brain through one or more cerebral veins 20. The elongated body 510 may include a conduit extending therethrough that is capable of sliding over the guide wire 530. As such, the distal end 512 of the elongated body 510 may include a conduit opening to receive the proximal end (not shown in FIGS. 5A-B) of the guide wire 530. The user may then deliver the electrodes 520 and 522 to the targeted portion by sliding the elongated body 510 over the guide wire 530 toward the distal end 532 of the guide wire 530. In these embodiments, the outer diameter of the elongated body 510 may be sized to safely pass through the inside of various cerebral veins 20.

In one exemplary implementation, a user may be able to analyze an electrophysiological map of a patient's brain 10 and, at the same time or within a short time period before or after the mapping process, may be able to apply ablation energy for treatment of a nervous system disorder. As shown in FIGS. 5A-B, the mapping-ablation electrode device 500 may percutaneously enter the venous system through the patient's jugular vein, and the distal end 512 may be guided over the wire 530 through one or more cerebral veins 20 toward a targeted portion of the patient's brain 10. (In this embodiment, the distal end 512 is directed to a temporal lobe portion of the brain 10.) The user may direct the electrodes 520 and 522 to different portions of the brain 10 using the guide wire 530. In those different brain portions, the user may employ the electrodes 520 and 522 to detect the electrophysiological signals to map at least a portion of the brain 10 using, for example, an electrophysiological mapping and display system (e.g., a digital EEG display system or the like). If the mapping process does not reveal a portion of the brain 10 that is affected by a nervous system disorder or that otherwise requires treatment, the user may direct the electrodes 520 and 522 to a different portion of the brain 10.

If the mapping process reveals a portion of the brain 10 that is affected by a nervous system disorder of otherwise requires treatment, the user may thereafter deliver ablation energy to the affected tissue using the electrodes 520 and 522. For example, as shown in FIGS. 5A-B, if the mapping process determines the location of an electrical event (e.g., a seizure focus 515) in the brain 10, the electrodes 520 and 522 may be used to delivery RF ablation energy to the brain tissue in the affected portion of the brain. Accordingly, in some embodiments, a user may view a high-resolution map of at least a portion of the patient's brain and may contemporaneously treat that portion of the brain with ablation energy, all of which may be accomplished without an invasive procedure that requires an opening to be formed in the patient's cranium.

In some circumstances, the guide wire 530 may be removed from the inner conduit of the elongated body 510 after the electrodes 520 and 522 are delivered to a targeted portion of the brain 10. Then, the inner conduit may be used to deliver a medicament delivery catheter (not shown in FIGS. 5A-B), such as a syringe catheter that is capable of dispensing a controlled amount of a medicament or other chemical. For example, the inner conduit of the elongated body may be used to direct a syringe catheter containing a chemical solution used to treat the body tissue after the ablation process. In another example, the electrodes may be used to map a particular portion of the brain so as to identify a vascular event (e.g., a stroke) or an electrical event (e.g., a seizure) in which the selected treatment may require dispersion of medicament or other chemical without the use of ablation. In these examples, the guide wire 530 and the inner conduit of the elongated body 510 may be employed to deliver the electrodes 520 and 522 to a targeted brain portion, and the inner conduit may also be employed (after the guide wire 530 is removed) to deliver a controlled amount of medicament or other chemical to that portion of the brain 10. Additionally, for these types of uses, an embodiment with an inflatable balloon (not pictured) to force medication diffusion in a particular direction in a vessel may be useful. The balloon may occlude a vein while medication is delivered distal to the balloon site, preventing blood flow from dispersing the therapeutic agent away from the target region.

Referring to FIGS. 6A-E, a mapping-ablation device 600 may be adapted to penetrate a cerebral vein 20 so as to deliver electrodes 620 and 622 through the wall of the cerebral vein 20 and into the brain tissue 30. In this embodiment, the device 500 includes two electrodes 620 and 622 that are capable of detecting electrophysiological signals in a portion of a brain 10, capable of detecting impedance parameters in a portion of the brain 10, or both. The elongated body 610 may comprise a flexible catheter having an inner conduit through which one or more electrical wires or conductive lines (not shown in FIGS. 6A-E) may pass. The electrical wires may extend through the elongated body 610 so as to electrically couple to the electrodes 620 and 622, and the electrical wires may extend out of a proximal end (not shown in FIGS. 6A-E) of the elongated body 610 so as to electrically couple with a control unit, such as an electrophysiological mapping control and display system or an implantable control unit.

As previously described, the guide wire 630 may comprise a flexible, biocompatible material having a distal end 632 (FIG. 6C) that is steerable or may be controllably bendable. As such, the guide wire 630 may percutaneously enter the patient's jugular or femoral vein and then may be directed to a targeted portion of the brain through one or more cerebral veins 20. The elongated body 610 may include an inner conduit extending therethrough that is capable of sliding over the guide wire 630. The user may then deliver the electrodes 620 and 622 to the targeted portion by sliding the elongated body 610 over the guide wire 630 toward the distal end 632 of the guide wire 630. In these embodiments, the outer diameter of the elongated body 610 may be sized to safely pass through the inside of various cerebral veins 20.

Referring to FIGS. 6B-E, the mapping ablation device 600 may include a needle device 635 configured to slide over the guide wire 630 so as to puncture the wall of a cerebral vein 20. A user may direct the needle device 635 to form an opening 25 in the vein 20 so that the guide wire 630 may pass through the wall of the vein 20 into the brain tissue 30. In general, the needle device 635 may be wholly or partially withdrawn away from opening 25 in the vein 20 before the guide wire 630 is directed into the brain tissue 630 (refer to FIG. 6C). The distal end 612 of the elongated body 610 may be directed over the guide wire 630 through the opening 25 an into the brain tissue 30. In some embodiments, the electrodes 620 and 622 may be positioned to directly contact the brain tissue 30. As previously described in other embodiments, the user may be able to analyze an electrophysiological map of a patient's brain 10 and, at the same time or within a short time period before or after the mapping process, may be able to apply ablation energy for treatment of a nervous system disorder. In this embodiment, the electrodes 620 and 622 may be in direct contact with the brain tissue 30 during the mapping process and during the ablation process. In such circumstances, the brain tissue 30 that requires ablation treatment may be locally ablated with a reduced likelihood of unnecessarily ablating non-targeted tissue. As shown in FIG. 6E, the opening 25 formed in the cerebral vein 20 may wholly or partially sealed by delivering ablation energy to the opening 25 after the electrodes 620 and 622 have been withdrawn from the brain tissue 30 and into the vein 20. The ablation energy from the electrodes 620 and 622 in the vein 20 may cause the opening 25 in the vein to effectively seal, thereby preventing excessive blood flow from the vein 20 into the brain tissue 30.

As previously described, the user may direct the electrodes 620 and 622 to different portions of the brain 10 using the guide wire 630 (and using the needle device 635 when there is a need to penetrate through the cerebral vein 20 into the brain tissue 30). In those different brain portions, the user may employ the electrodes 620 and 622 to detect the electrophysiological signals to map at least a portion of the brain 10 using, for example, an electrophysiological mapping and display system (e.g., a digital EEG display system or the like). If the mapping process does not reveal a portion of the brain 10 that is affected by a nervous system disorder or that otherwise requires treatment, the user may direct the electrodes 620 and 622 to a different portion of the brain 10.

If the mapping process reveals a portion of the brain 10 that is affected by a nervous system disorder of otherwise requires treatment, the user may thereafter deliver ablation energy to the affected tissue (e.g., brain tissue 30) using the electrodes 620 and 622. Accordingly, in some embodiments, a user may view a high-resolution map of at least a portion of the patient's brain and may contemporaneously treat that portion of the brain with ablation energy, all of which may be accomplished without an invasive procedure that requires an opening to be formed in the patient's cranium. As previously described, various imaging modalities can be used to identify the location of electrodes 620 and 622 relative to other electrodes and anatomic structures.

Also as previously described, the guide wire 630 may be removed from the inner conduit of the elongated body 610 after the electrodes 620 and 622 are delivered to a targeted portion of the brain 10. Then, the inner conduit may be used to deliver a medicament delivery catheter (not shown in FIGS. 6A-E), such as a syringe catheter that is capable of dispensing a controlled amount of a medicament or other chemical.

Figure 7A:
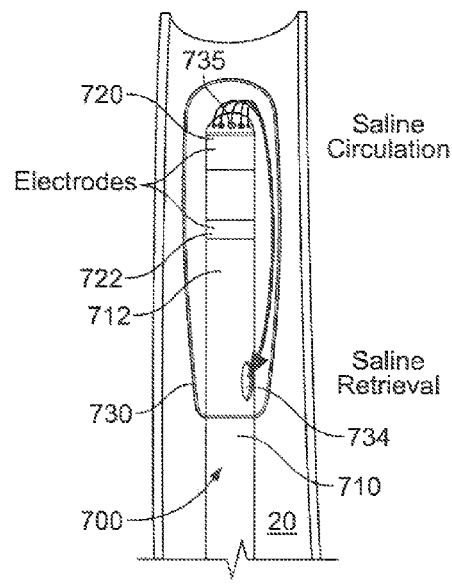
FIGS. 7A-C are magnified views of some embodiments of a mapping-ablation device.

Referring to FIG. 7A, a mapping-ablation device 700 may include an inflatable balloon structure 730 that permits the both internal and external cooling of the device 700. In this embodiment, the device 700 includes two electrodes 720 and 722 that are capable of detecting electrophysiological signals in a portion of a brain 10, capable of detecting impedance parameters in a portion of the brain 10, or both. The elongated body 710 may comprise a flexible catheter having a conduit through which one or more electrical wires or conductive lines (not shown in FIG. 7A) may pass. The electrical wires may extend through the elongated body 710 so as to electrically couple to the electrodes 720 and 722, and the electrical wires may extend out of a proximal end (not shown in FIG. 7A) of the elongated body 710 so as to electrically couple with a control unit, such as an electrophysiological mapping control and display system or an implantable control unit. As previously described, the distal end 712 of the elongated body 710 may be steerable (e.g., via steering wires or via a guide wire) so that the electrodes 720 and 722 may be directed through one or more cerebral veins 20 to a target portion of the brain. In some embodiments, the electrodes 720 and 722 may be capable of delivering RF ablation energy. For example, electrodes 720 and 722 may comprise opposite poles such that resistive heating occurs between the electrodes 720 and 722. In another example, the electrodes 720 and 722 may interact with an opposite electrode pole disposed elsewhere so that resistive heating occurs between the saline solution in the balloon structure 735 (charged by the electrodes 720 and 722) and the opposite electrode pole (described in more detail below).

The balloon structure 730 may comprise a flexible material that can be inflated from a first, non-expanded state to a second, expanded state. When the balloon structure 730 is in the expanded state, the balloon structure 730 may abut all or a portion of the vein wall 20. The elongated body 710 may include an input conduit extending therethrough so that a liquid (e.g., a saline solution) flows toward the balloon structure 730. The input conduit may terminate near the distal end 712 of the elongated body 710 at one or more fluid input ports

735. The fluid input ports direct the liquid (e.g., the saline solution) into the balloon structure 730 so as to expand the balloon. The liquid flows through the balloon volume and into at least one fluid exit port 734. The fluid exit port 734 is in fluid communication with a drain conduit that extends through the elongated body 710 so as to drain the liquid from the balloon. The flow of liquid through the balloon may be controlled so as to maintain the balloon in the expanded state.

The liquid may be cooled to a temperature below the body temperature of the patient (e.g., may be cooled to room temperature) so that as the fluid flows internally through the elongated body 710, the elongated body may be substantially continuously cooled. In addition, because the liquid flows outside of the elongated body 710 (inside the volume of the balloon structure 730, at least a portion of the outer area of the device 700 may be cooled (e.g., the outer area of the distal end 712 may be both internally and externally cooled). Because the device 700 includes such internal-external cooling action, the device may be capable of delivering more localized ablation heat energy while reducing the likelihood of unnecessarily ablating non-targeted tissue. For example, RF ablation energy may heat the surrounding tissue using resistive heating (e.g., when the RF energy encounters the higher impedance of human tissue, heat is produced). The internal-external cooling of the device 700 provides the opportunity to delivering greater total energy to the targeted brain tissue without excessive heating along the outer surface of the electrodes 720 and 722. Such embodiments may increase the effectiveness of the ablation treatment and may reduce the likelihood of unnecessarily ablating healthy brain tissue.

Figure 7B:
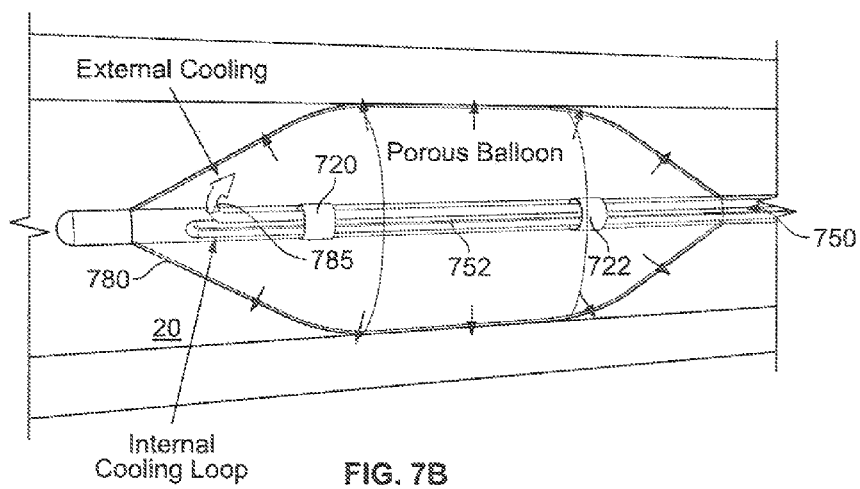
Figure 7C:
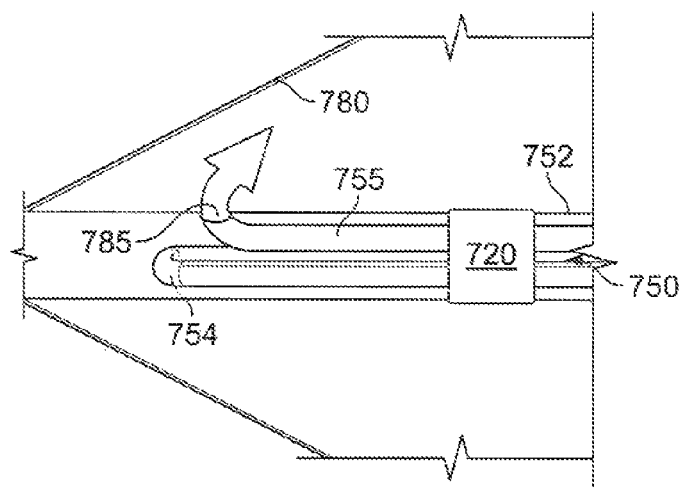

Referring to FIGS. 7B-C, some embodiments of a mapping-ablation device 750 may comprise a material that permits a limited amount of the liquid, such as the saline solution, to weep from the balloon structure 780. In this embodiment, the device 750 includes two electrodes 720 and 722 that are capable of detecting electrophysiological signals in a portion of a brain 10, capable of detecting impedance parameters in a portion of the brain 10, or both. The balloon structure 780 may comprise an flexible material that can be inflated from a first, non-expanded state to a second, expanded state. When the balloon structure 780 is in the expanded state, the balloon structure 780 may abut all or a portion of the vein wall 20. The device 750 may include an internal cooling conduit 754 (FIG. 7C) extending therethrough so that a liquid (e.g., a saline solution) circulates through the elongated body to internally cool the distal end 752. The internal cooling conduit 754 may loop near the distal end 752 so as to return toward the proximal end (not shown) of the device 750. The device 750 may also include an inflation fluid conduit 755 (FIG. 7C) extending therethrough so that a liquid (e.g., a saline solution) is directed toward the balloon structure 780. The inflation fluid conduit 755 may terminate at a port 785 near the distal end 752 so that fluid passing through the conduit 755 may inflate the balloon structure 780 and cause some portion of the fluid to weep from the balloon structure 780.

The electrodes 720 and 722 may act as a common pole that interacts with an opposite electrode pole disposed elsewhere (e.g., an electrode patch on the patient's scalp or an opposite electrode outside the balloon structure 780. In these circumstances, the liquid in the balloon structure 780 may comprise a saline solution (or other electrically conductive material) so that the saline solution in electrical communication with the electrodes 720 and 722 serves as a "common electrode pole" that interacts with the opposite electrode pole disposed elsewhere. Because the balloon structure 780 may comprise a material that permits a limited amount of the liquid to weep, the liquid that weeps from the balloon may further disperse the "common electrode pole" created when the saline solution is in electrical communication with the electrodes 720 and 722. For example, RF ablation energy can be delivered between the saline solution (both in the balloon 780 and weeping outside the balloon) and the opposite electrode pole disposed elsewhere so as to ablate a localized, targeted tissue area.

Figure 8A:
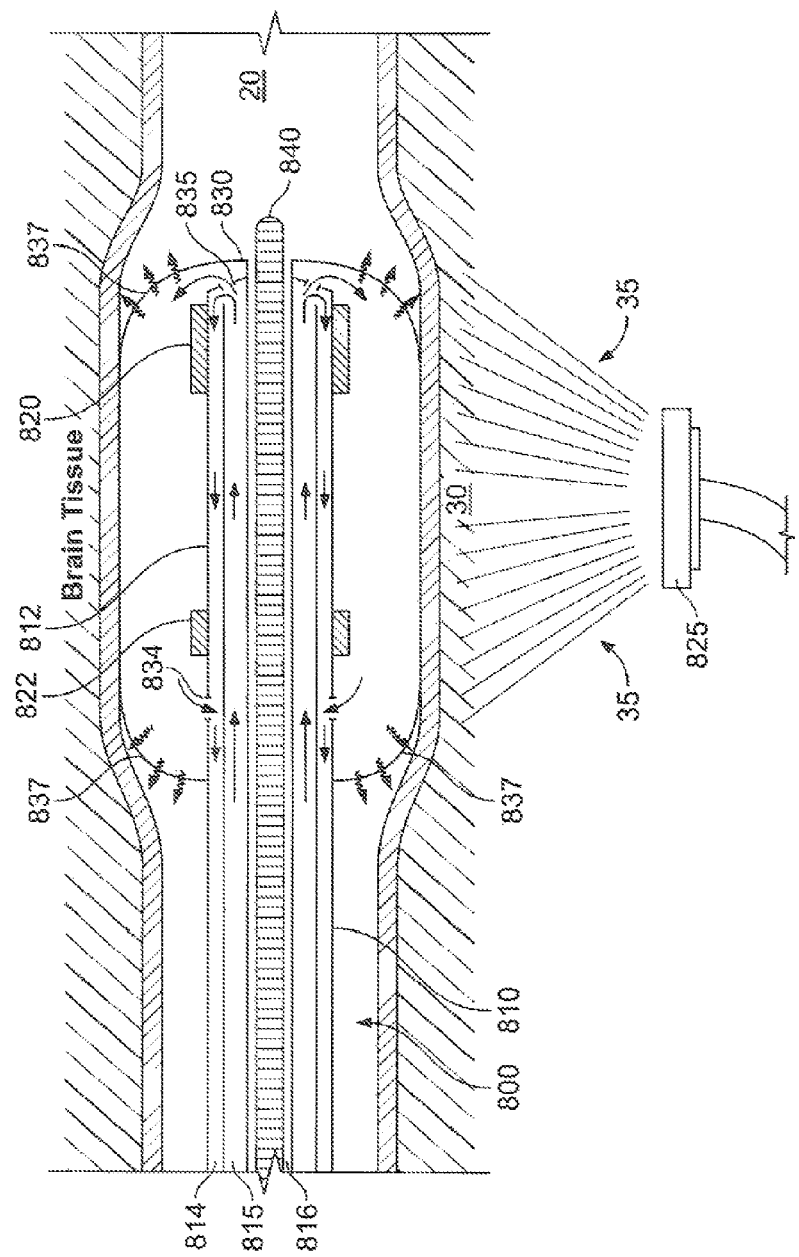
FIGS. 8A-B are cross-sectional views of other embodiments of a mapping-ablation device.

Referring now to FIG. 8A, a mapping-ablation device 800 having a balloon structure 830 may be directed to a target portion of the brain using a guide wire 840. In this embodiment, the device 800 includes two electrodes 820 and 822 that are capable of detecting electrophysiological signals in a portion of a brain 10, capable of detecting impedance parameters in a portion of the brain 10, or both. The elongated body 810 may comprise a flexible catheter through which one or more electrical wires or conductive lines (not shown in FIG. 8) may pass. The electrical wires may extend through the elongated body 810 so as to electrically couple to the electrodes 820 and 822, and the electrical wires may extend out of a proximal end (not shown in FIG. 8) of the elongated body 810 so as to electrically couple with a control unit, such as an electrophysiological mapping control and display system or an implantable control unit. The elongated body 810 may include an conduit 816 that is configured to slide over a guide wire 840. As such, the distal end 812 may by directed over the guide wire 840 so that the electrodes 820 and 822 can be directed through one or more cerebral veins 20 to a target portion of the brain.

As previously described, the balloon structure 830 may comprise an flexible material that can be inflated from a first, non-expanded state to a second, expanded state. When the balloon structure 830 is in the expanded state, the balloon structure 830 may abut all or a portion of the vein wall 20. The elongated body 810 may include an input conduit 815 extending therethrough so that a liquid (e.g., a saline solution) flows toward the balloon structure 830. The input conduit may terminate near the distal end 812 of the elongated body 810 at one or more fluid input ports 835. The fluid input ports direct the liquid (e.g., the saline solution) into the balloon structure 830 so as to expand the balloon. The liquid flows through the balloon volume and into one or more fluid exit ports 834. The fluid exit ports 834 are in fluid communication with a drain conduit 814 that extends through the elongated body 810 so as to drain the liquid from the balloon structure 830. The flow of liquid through the balloon structure 830 may be controlled so as to maintain the balloon structure 830 in the expanded state. The liquid may be cooled to a temperature below the body temperature of the patient (e.g., may be cooled to room temperature) so that the device 800 provides an internal-external cooling action, as previously described.

In some embodiments, the electrodes 820 and 822 may act as a common pole that interacts with an opposite electrode pole disposed elsewhere. The opposite electrode pole may be part of an electrode patch 825 disposed on the patient's scalp. As such, the brain tissue between electrodes 820 and 822 and the electrode patch 825 may be targeted for ablation therapy. In these circumstances, the liquid in the balloon structure 830 may comprise a saline solution (or other electrically conductive material) so that the saline solution in electrical communication with the electrodes 820 and 822 serves as a "common electrode pole" that interacts with the opposite electrode pole of the electrode patch 825. The RF ablation energy can be delivered between the saline solution in the balloon structure 830 and the electrode patch 825, thereby dispersing the ablation energy in a localized, targeted tissue area 35. As previously described, RF ablation energy may heat the targeted tissue using resistive heating (e.g., when the RF energy encounters the higher impedance of human tissue, heat is produced). The internal-external cooling of the device 800 provides the opportunity to delivering greater total energy to a localized area 35 of brain tissue without excessive heating along the outer surface of the electrodes 820 and 822. Such embodiments may increase the effectiveness of the ablation treatment and may reduce the likelihood of unnecessarily ablating healthy brain tissue.

It should be understood that the electrodes 820 and 822 or other portion of the mapping-ablation device 800 may be configured to deliver one more types of ablation energy, including RF energy, ultrasound energy, and microwave energy. In some embodiments, the mapping-ablation device 800 may be configured to deliver various types of energy (e.g., RF energy, ultrasound energy, microwave energy, and the like) simultaneously or sequentially to targeted portions of the brain.

In some embodiments, the balloon structure 830 may comprise a material that permits a limited amount of the liquid, such as the saline solution, to weep 837 from the balloon structure 830. In such circumstances, the liquid that weeps from the balloon may further disperse the "common electrode pole" created when the saline solution is in electrical communication with the electrodes 820 and 822. In other words, the RF ablation energy can be delivered between the saline solution (both in the balloon and weeping outside the balloon) and the electrode patch 825 to ablate a localized, targeted tissue area 35. The "common electrode pole" may be effectively widened by the weeping 837 saline solution so as to promptly distributed the ablation energy to controlled area 35 without having to reposition the balloon structure 830 in the vein. Additionally, different liquids could be selected for use depending on the clinical situation, differentially affecting the size of the ablative lesion. Hypertonic solutions, for example, which are excellent electrical conductors, could be employed when larger lesion size is desired.

It should be understood that, in other embodiments, the device may not employ an opposite electrode pole (e.g., electrode patch 825) disposed outside of the balloon structure 830. For example, the electrodes 822 and 820 may be used to deliver RF ablation energy while the electrodes are in contact with the liquid in the balloon structure 830, thereby causing the liquid in the balloon structure 830 to serve as an ablation delivery instrument In such circumstances, the heat generated from resistance in the liquid may be delivered to the brain tissue 30 through the saline solution.

Figure 8B:
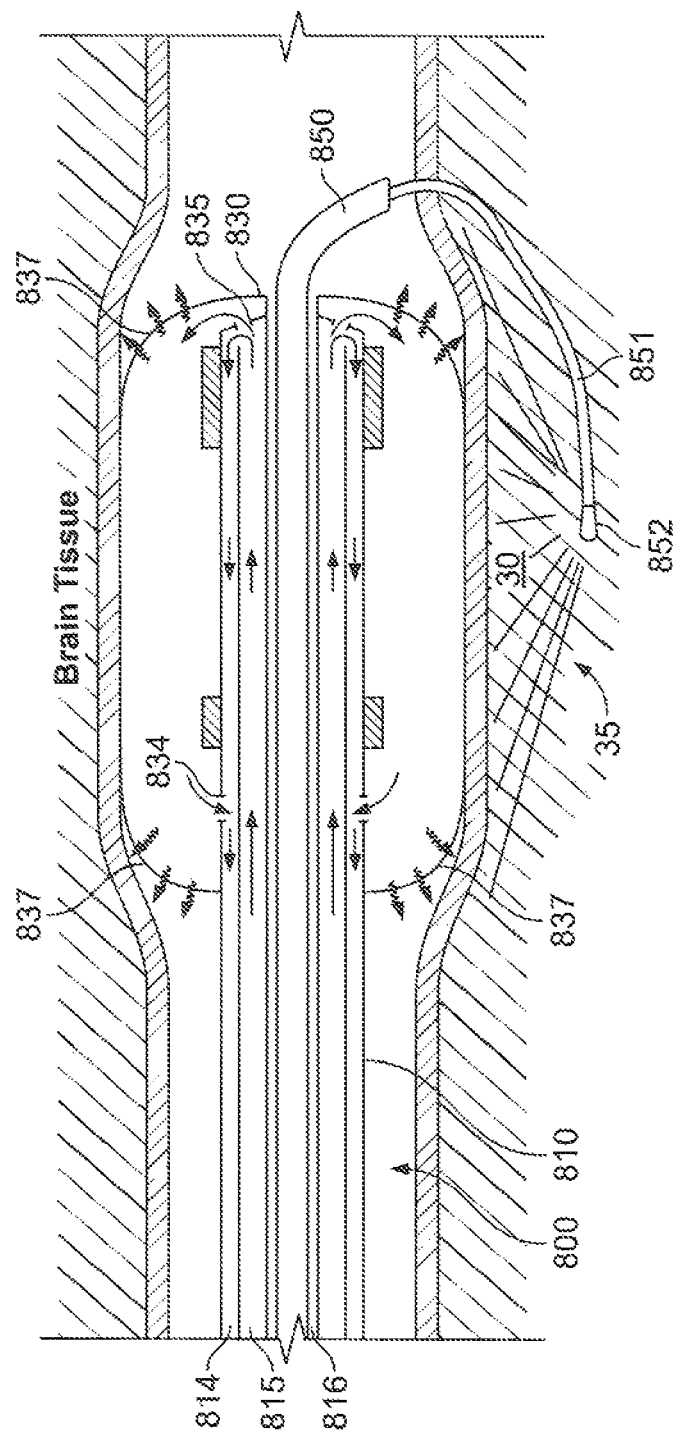

Referring now to FIG. 8B, the mapping-ablation device 800 may include an opposite pole electrode 852 that can be disposed in a position spaced apart from the electrodes 820 and 822. The opposite pole electrode 852 may be capable of more accurately directing the ablation energy to a localized area 35 of the brain tissue 30. In one exemplary implementation, the guide wire 840 (FIG. 8A) may be withdrawn from the conduit 816 so that an electrode delivery sheath 850 may be passed therethrough. The electrode delivery sheath 850 may include a conduit through with the electrode rod 851 is passed. The opposite pole electrode 852 may be disposed near a distal end of the rod 851 such that the position of the electrode 852 may be adjusted by shifting the rod 851 within the delivery sheath 850.

The opposite pole electrode 852 may be adapted to pass through the wall of the cerebral vein 20 and into the brain tissue 30 to provide more accurate direction of the ablation energy to a localized area 35 of the brain tissue 30. For example, the electrode 852 may include a needle-like tip that permits the electrode 852 to puncture the vein wall. In another example, the delivery sheath 850 may include a needle device (similar to needle device 635 of FIG. 6B) to puncture the vein wall. The electrode rod 851 may be steerable or may comprise a shape-memory member (to cause a bend when the rod 851 is outside the sheath 850) so that the opposite pole electrode 852 may be directed into the brain tissue 30. The opposite pole electrode 852 may be electrically coupled to a wire or a conductive line that extends through the rod 851 to a proximal end (not shown in FIG. 8B) for connection to a control unit.

In this embodiment, the mapping-ablation device 800 delivers ablation energy to the localized area 35 of brain tissue between the electrodes 820 and 822 and the opposite pole electrode 852. A user may shift the selected area to be ablated by shifting the position of the opposite pole electrode 852 relative to the distal end 812 (e.g., where the electrodes 820 and 822 are disposed). In these circumstances, the liquid in the balloon structure 830 may comprise a saline solution (or other electrically conductive material) so that the saline solution in electrical communication with the electrodes 820 and 822 serves as a "common electrode pole" that interacts with the opposite pole electrode 852. The RF ablation energy can be delivered between the saline solution in the balloon structure 830 and the opposite pole electrode 852, thereby dispersing the ablation energy in a localized, targeted tissue area 35. As previously described, RF ablation energy may heat the targeted tissue using resistive heating (e.g., when the RF energy encounters the higher impedance of human tissue, heat is produced). The internal-external cooling of the device 800 provides the opportunity to delivering greater total energy to a localized area 35 of brain tissue without excessive heating along the outer surface of the electrodes 820 and 822. Such embodiments may increase the effectiveness of the ablation treatment and may reduce the likelihood of unnecessarily ablating healthy brain tissue.

Figure 9A:
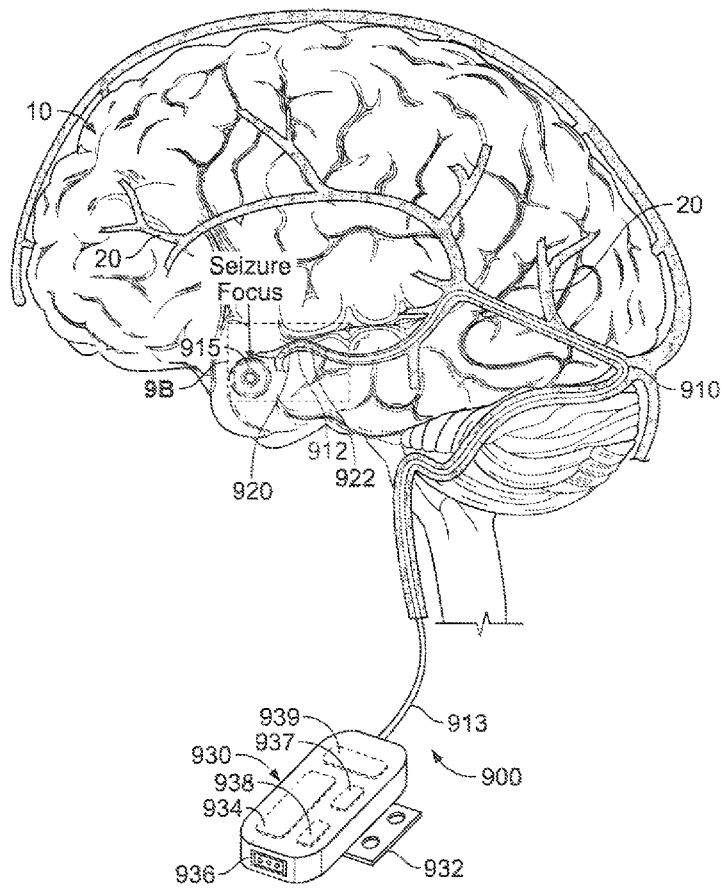
FIG. 9A-B is a side view of another embodiment of a mapping-ablation device and an implantable control unit.
Figure 9B:
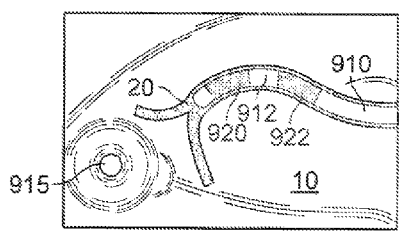

Referring to FIGS. 9A-B, a mapping-ablation device 900 may be coupled to an implantable control unit 930 configured to monitor the electrophysiological signals and/or impedance parameters in the brain 10 and configured to respond to those signals and/or parameters. In this embodiment, the device 900 includes at least one elongated body 910 having one or more electrodes 920 and 922 disposed near a distal end 912 of the body 910. (It should be understood, that the device 900 may include a plurality of elongated bodies similar to the embodiment described in connection with FIG. 2.) The electrodes 920 and 922 may be capable of detecting electrophysiological signals in a portion of a brain 10, capable of detecting impedance parameters in a portion of the brain 10, or both. The elongated body 910 may comprise a flexible catheter having a conduit through which one or more electrical wires or conductive lines (not shown in FIG. 9) may pass. The electrical wires may extend through the elongated body 910 so as to electrically couple to the electrodes 920 and 922, and the electrical wires may extend out of a proximal end 913 of the elongated body 910 so as to electrically couple with a control unit, such as the implantable control unit 930. The distal end 912 of the elongated body 910 may be steerable (e.g., via steering wires or via a guide wire) so that the electrodes 920 and 922 may be directed through one or more cerebral veins 20 to a target portion of the brain, including portions in the frontal lobe, parietal lobe, occipital lobe, temporal lobe, thalamus, hypothalamus, and the like. For example, the distal end 912 of at least one elongated body 910 may be delivered to a targeted portion of the temporal lobe where a seizure focus is known or predicted to exist in a patient's brain, and in such circumstances the mapping-ablation device 900 may be capable of detecting an treating the seizure-causing condition. In another example, the distal end 912 of the elongated body 910 may be delivered to the hypothalamus to ablate or stimulate neurons in the arcuate nucleus of the hypothalamus, which may be effective to treat obesity or other conditions.

The implantable control unit 930 may be configured to be implanted proximal to the patient's clavicle (not shown) of another portion of the patient's body. For example, the control unit 930 may include a mounting plate 932 that is configured to receive bone screws for mounting to the clavicle or to receive an engagement cable for wrapping around a portion of the clavicle. The control unit 930 may have an outer shape that is adapted to abut along a portion of the clavicle or along another portion of the patient's body. The control unit may be surgically implanted after the electrodes 920 and 922 have been directed to a targeted portion of the brain using, for example, a percutaneous entry through the patient's jugular vein. After the electrodes 920 and 922 have been properly positioned in the patient's brain, the proximal end 913 of the elongated body 910 may be connected to the control unit 930 (either before or after the control unit is mounted to the clavicle or other body portion).

The control unit 930 may include a power source 934 that provides electrical energy to the various components of the control unit 930. In some circumstances, the power source 934 may also provide electrical energy to the electrodes 920 and 922 for purposes of stimulating tissue or for purposes of ablating tissue. The power source 934 may comprise a battery device or the like. In some circumstances, the power source may be periodically recharged using a wireless inductive coil.

In some embodiments, the control unit 930 may include a data port 936 to connect with a cable or other jack so that data may be transferred to or from the control unit 930. In some embodiments, the control unit may include software and filter settings that may be updated or otherwise adjusted, depending on the patient's needs. In those circumstances, the data port 936 may be used to communicate data to or the control unit 930.

The control unit 930 may include a wireless transmitter 937, a wireless receiver 938, or both. The wireless transmitter 937 may be configured to transmit a signal when a predetermined parameter or set of parameters is detected. For example, the electrodes 920 and 922 may detect electrophysiological signals, impedance parameters, or both and such data may be received by the control unit 930. The control unit 930 may include one or more controller circuits that use this data to predict an impending vascular event (e.g., a stroke), an electrical event (e.g., a seizure), or both, as described in more detail below. In response thereto, the control unit 930 may employ the transmitter 937 to send a signal that can be used to alert the patient of the imminent event (e.g., a stroke or seizure), contact emergency care providers, or the like. The wireless receiver 938 may be employed to receive updates or modifications to the control units internal settings or software, to receive a command sent from a communication device outside the patient's body (e.g., a command to stimulate the brain 10 using the electrodes 920 and 922), or both.

Still referring to FIGS. 9A-B, the control unit 930 may also include controller circuit 939 configured to receive data signals from the electrodes 920 and 922 and to initiate a response to those data signals if predetermined parameters are met. In one non-limiting example, the controller circuit 939 may include at least one filter that electrically filter the data signals received from the electrodes 920 and 922 in the brain 10 and that output. In some embodiments, the filter may be an open filter having a high pass of 20 MHz and a low pass of 400 to 500 MHz. In this non-limiting example, the filter amplitude may be about 0.05 mvolts to about 4 mvolts and the filter slew may be approximately 0.3 to approximately 3 mvolts/msec. As previously described, the data port 936 of the wireless receiver 938 may be used to update or adjust these filter settings depending on the particular portion of the brain that is being mapped. In some embodiments, the filter may be controlled by a dynamic algorithm that will set the proper parameters based upon the location of the electrodes 920 and 922 in the brain 10.

The controller circuit 939 may comprise integrated circuits, software stored on computer memory, or other components that are programmed to predict an imminent vascular event (e.g., a stroke), electrical event (e.g., a seizure), or both based upon the data signals from the electrodes 920 and 922 in the brain 10. In some instances, the electrophysiological signals in the brain 10, the impedance parameters in the brain, or both may become measurably abnormal in the moments before a vascular event (e.g., a stroke) or electrical event (e.g., a seizure). The controller circuit 939 or other portion of the control unit 930 may process the incoming signals to monitor the brain activity. The controller circuit 939 may comprise a computer memory unit that stored data indicating normal brain activity. The controller circuit 939 may be configured to receive data signals from the electrodes 920 and 922 and to compare the data signals with normal brain activity data stored by the control unit 930. If abnormal signals or parameters are detected by the electrodes 920 and 922, the controller circuit 939 or other portion of the control unit 930 may respond. For example, a change in the threshold signal of 30 to 60% may indicate abnormal signals or parameters that triggers a response from the control unit 930.

The controller circuit 939 or other portion of the control unit 930 may respond to abnormal signals or parameters in a number of ways. For example, the control unit 930 may be configured to transmit a signal that alerts the patient or a nearby receiver that an imminent vascular event (e.g., a stroke) or electrical event (e.g., a seizure) may occur. Such an alert may prompt the patient or another person to contact emergency care providers for help. Types of alerts may include an audible tone generated by the control unit 930 or an associated device, a small shock, or communication with a cell phone or other wireless communication device. In another example, the control unit 930 may be configured to transmit a signal to an emergency care provider or to a monitoring station that indicates the patient's geographical location (e.g., the control unit 930 may be configured to transmit data associated with the patient's global positioning coordinates or other GPS system). In a further example, the control unit 930 may respond to abnormal signals or parameters detected in the brain 10 by causing a pacing stimulation signal to be delivered to the electrodes 920 and 922. The pacing stimulation signal may attempt to restore normal electrical activity in the brain 10 by electrically stimulating at a predetermined frequency (e.g., at approximately 80% of the intrinsic frequency). In another example, the control unit 930 may be configured to apply a defibrillator shock or rapid pacing via the electrodes 920 and 922 in the brain 10. This therapeutic electrical therapy may be configured to terminate seizure events. In yet another example, the device 900 may include an inner conduit with a preset amount of medicament or other chemical (e.g., a thrombolytic) so that the control unit 930 may be configured to release the medicament or other chemical (e.g., a thrombolytic) to the portion of the brain near the electrodes 920 and 922. The medicament or other chemical (e.g., a thrombolytic) may be effective at treating the vascular event (e.g., a stroke) or electrical event (e.g., a seizure) until the patient receive further medical care.

It should be understood that the control unit 930 may wireless communicate with the electrodes 920 and 920 rather than using a wired connection via the elongated body 910. In such embodiments, the proximal end 513 of the elongated body 510 may be connected with the control unit 930. Rather, a substantial portion of the elongated body 910 may be removed from the patient's body while the electrodes 920 and 922 and other components remain in the brain 10. It should also be understood that in addition to monitoring electrical signals from within nervous tissue, the control unit may be used to detect embolic events. For example, the control unit may employ ultrasound interrogation of vascular structures (e.g., carotid artery) adjacent to the veins (e.g., jugular vein) in which the elongated body resides.

A number of embodiments of the invention have been described. Nevertheless, it will be understood that various modifications may be made without departing from the spirit and scope of the invention. Accordingly, other embodiments are within the scope of the following claims.

What is claimed is:

1. A method of using a catheter device to provide intravenous brain mapping from within one or more cerebral veins, comprising:

advancing a distal tip portion of a brain mapping catheter device through a patient's vein that extends below the patient's head to a first position within one or more cerebral veins proximal to brain tissue within the patient's head, wherein the brain mapping catheter device accesses the one or more cerebral veins without surgical access through an opening in the patient's cranium;

using one or more electrodes positioned along the distal tip portion of the brain mapping catheter device to detect first electrophysiological signals in a portion of the brain tissue while the one or more electrodes remain disposed at the first position within the one or more cerebral veins and while a proximal portion of the brain mapping catheter device resides external to the patient;

after viewing the first electrophysiological signals being displayed on an electrophysiological mapping control and display system, directing the distal tip portion of the brain mapping catheter device to a second position within one or more cerebral veins proximal to the brain tissue; and using the one or more electrodes positioned along the distal tip portion of the brain mapping catheter device to detect second electrophysiological signals in the brain tissue while the one or more electrodes remain disposed at the second position within the one or more cerebral veins, the second electrophysiological signals being indicative of a location of a seizure focus and being displayed on the electrophysiological mapping control and display system.

2. The method of claim 1, further comprising electrically coupling at least one component of the proximal portion of the brain mapping catheter device to an electrophysiological mapping control and display system.

3. The method of claim 2, wherein the brain mapping catheter device comprises a flexible elongated body having an internal conduit through which one or more electrical wires or conductive lines pass and electrically couple to the one or more electrodes along the distal tip portion of the brain mapping catheter device, the electrical wires extending to the proximal portion of the brain mapping catheter device so as to electrically couple with the electrophysiological mapping control and display system.

4. The method of claim 2, further comprising viewing one or more electrogram signals displayed by the electrophysiological mapping control and display system in response to the one or more electrodes detecting the electrophysiological signals in the portion of the brain tissue.

5. The method of claim 1, further comprising using said one or more electrodes positioned along the distal tip portion of the brain mapping catheter device to provide electrical therapy to the portion of the brain.

6. The method of claim 5, wherein the electrical therapy output from the one or more electrodes at the portion of the brain comprises electrical ablation energy.

7. The method of claim 5, wherein the one or more electrodes are longitudinally spaced apart along the distal tip portion of the brain mapping catheter device electrodes so as to provide contemporaneous mapping and electrical therapy at the portion of the brain tissue due to the signals detected by the electrodes and due to the electrical energy output from the electrodes.

8. The method of claim 1, wherein the one or more electrodes comprise a first electrode and a second electrode longitudinally spaced apart from the first electrode along the distal tip portion, wherein the first and second electrodes are: configured to detect electrophysiological signals in the portion of the brain tissue, configured to detect impedance parameters in the portion of the brain tissue, or both.

9. The method of claim 1, wherein the step of advancing the distal tip portion of the brain mapping catheter device comprises advancing the distal tip portion through the patient's femoral vein or jugular vein that extends below the patient's head and to the position within the one or more cerebral veins proximal to brain tissue within the patient's head.

10. The method of claim 1, wherein the brain mapping catheter device comprises:

a flexible elongated body defining a fluid input conduit in fluid communication with a fluid input port near the distal tip portion and defining a drain conduit in fluid communication with a drain port near the distal tip portion; and a balloon structure disposed near the distal tip portion so as to surround the fluid input port, the drain port, and the one or more electrodes, the balloon structure being adjustable from a non-expanded state to an expanded state when a fluid flows from the input port and to the drain port.

11. The method of claim 10, further comprising delivering fluid flow from the input port and to the drain port of the brain mapping catheter device while the flexible elongated body is internally cooled by fluid flow through the fluid input conduit and is externally cooled along at least a portion of the distal tip portion surround by the balloon.

12. The method of claim 1, further comprising electrically coupling at least one component of the proximal portion of the brain mapping catheter device to an electrophysiological mapping control and display system such that the one or more electrodes are electrically connected to the electrophysiological mapping control and display system, wherein the electrophysiological mapping control and display system displays one or more electrogram signals in response to the one or more electrodes detecting the electrophysiological signals in the portion of the brain tissue, and wherein the electrophysiological mapping control and display system outputs ablation energy via the one or more electrodes along the distal tip portion of the brain mapping catheter device.

13. The method of claim 12, wherein when the electrophysiological mapping control and display system outputs ablation energy via the one or more electrodes, the one or more electrodes along the distal tip portion interact with an opposite pole electrode disposed outside the cerebral vein so as to ablate at least a portion of brain tissue between the one or more electrodes and the opposite pole electrode.

14. The method of claim 1, further comprising advancing a guide wire through the patient's vein that extends below the patient's head to the position within the one or more cerebral veins proximal to the brain tissue within the patient's head, wherein the brain mapping catheter device comprises a flexible elongated body defining a lumen to receive the guide wire when the distal tip portion of the brain mapping catheter device is advanced to the position within the one or more cerebral veins proximal to the brain tissue.

15. The method of claim 1, further comprising advancing a second distal tip portion of a second brain mapping catheter device to a second cerebral vein proximal to a third portion of brain tissue within the patient's head, wherein the second brain mapping catheter device accesses the second cerebral vein without surgical access through an opening in the patient's cranium.

16. A method of using a catheter device to provide intravenous brain mapping from within one or more cerebral veins, comprising:

advancing a distal tip portion of a brain mapping catheter device through a patient's vein that extends below the patient's head to a position within one or more cerebral veins proximal to brain tissue within the patient's head, wherein the brain mapping catheter device accesses the one or more cerebral veins without surgical access through an opening in the patient's cranium;

using one or more electrodes positioned along the distal tip portion of the brain mapping catheter device to detect electrophysiological signals in a portion of the brain tissue while the one or more electrodes remain disposed within the one or more cerebral veins and while a proximal portion of the brain mapping catheter device resides external to the patient;

advancing a second distal tip portion of a second brain mapping catheter device to a second cerebral vein proximal to a different portion of brain tissue within the patient's head, wherein the second brain mapping catheter device accesses the second cerebral vein without surgical access through an opening in the patient's cranium; and using one or more electrodes positioned along the second distal tip portion of the second brain mapping catheter device to detect electrophysiological signals in the different portion of the brain tissue while the one or more electrodes along the second distal tip portion remain disposed within the second cerebral vein, wherein the one or more electrodes of the second brain mapping catheter device are used to detect electrophysiological signals in the different portion of the brain tissue while simultaneously the one or more electrodes of the first brain mapping catheter device are used to detect electrophysiological signals in the first portion of the brain tissue.

17. The method of claim 16, further comprising electrically coupling at least one of the first and second brain mapping catheter devices to an electrophysiological mapping control and display system.

18. The method of claim 17, further comprising viewing one or more electrogram signals displayed by the electrophysiological mapping control and display system in response to the one or more electrodes of said at least one of the first and second brain mapping catheter devices detecting the electrophysiological signals.

19. The method of claim 16, further comprising using said one or more electrodes of at least one of the first and second brain mapping catheter devices to provide electrical ablation energy to the brain.

\* \* \* \* \*

UNITED STATES PATENT AND TRADEMARK OFFICE
CERTIFICATE OF CORRECTION

| | | |
|---|---|---|
| PATENT NO. | : 8,812,099 B2 | Page 1 of 1 |
| APPLICATION NO. | : 13/679167 | |
| DATED | : August 19, 2014 | |
| INVENTOR(S) | : Samuel J. Asirvatham et al. | |

It is certified that error appears in the above-identified patent and that said Letters Patent is hereby corrected as shown below:

On the Title Page, Column 1, item (72) Inventors, please delete "David R. Holmes, Rochester, MN (US)" and insert -- David R. Holmes, Jr., Rochester, MN (US) --, therefor.

Signed and Sealed this
Twenty-fifth Day of November, 2014

Michelle K. Lee
*Deputy Director of the United States Patent and Trademark Office*